United States Patent
Watanabe et al.

(10) Patent No.: US 10,016,119 B2
(45) Date of Patent: Jul. 10, 2018

(54) OBJECTIVE OPTICAL SYSTEM (71) Applicant: OLYMPUS CORPORATION, Tokyo (JP)

(72) Inventors: Takeshi Watanabe, Tokyo (JP); Tadashi Hirata, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 12 days.

(21) Appl. No.: 15/421,754

(22) Filed: Feb. 1, 2017

(65) Prior Publication Data
US 2017/0135564 A1 May 18, 2017

Related U.S. Application Data

(63) Continuation of application No. PCT/JP2014/072868, filed on Sep. 1, 2014.

(51) Int. Cl.
*G02B 9/64* (2006.01)
*A61B 1/00* (2006.01)
(Continued)

(52) U.S. Cl.
CPC .......... *A61B 1/00188* (2013.01); *A61B 90/20* (2016.02); *G02B 9/64* (2013.01); *G02B 21/02* (2013.01); *G02B 23/2407* (2013.01)

(58) Field of Classification Search
CPC .......... G02B 21/02; G02B 21/33; G02B 9/64; G02B 23/2407; A61B 1/00188; A61B 90/20
(Continued)

(56) References Cited

U.S. PATENT DOCUMENTS 4,989,957 A 2/1991 Suzuki
5,132,845 A * 7/1992 Suzuki .................. G02B 21/02
359/656

(Continued)

FOREIGN PATENT DOCUMENTS

EP 2 028 519 A2 2/2009
EP 2 192 434 A1 6/2010
(Continued)

OTHER PUBLICATIONS

International Search Report dated Oct. 28, 2014 issued in PCT/JP2014/072868.

*Primary Examiner* — Evelyn A Lester
(74) *Attorney, Agent, or Firm* — Scully, Scott, Murphy & Presser, P.C.

(57) ABSTRACT

Provided is an objective optical system composed of, in order from an object side, a first and a second groups, the first group including: a positive and single lens having a flat surface on an object side and a convex surface directed toward an image plane; a positive and single lens having a convex surface directed toward an object; a positive lens in which a convex lens having a flat surface directed toward the object and a negative lens are cemented, and the second group including: a lens in which a negative lens and a double-convex lens are cemented; a lens in which a lens having a concave surface directed toward the object and a lens having a convex surface directed toward the object are cemented; a negative lens in which a negative lens, a positive lens, and a negative lens are cemented; and a positive and compound lens.

4 Claims, 12 Drawing Sheets

(51) Int. Cl.
 *G02B 21/02* (2006.01)
 *G02B 23/24* (2006.01)
 *A61B 90/20* (2016.01)

(58) Field of Classification Search
 USPC .............................. 359/656, 657, 755, 798
 See application file for complete search history.

(56) References Cited

U.S. PATENT DOCUMENTS

| | | | | |
|---|---|---|---|---|
| 5,469,299 | A * | 11/1995 | Nagano | G02B 13/143 359/355 |
| 6,392,814 | B1 * | 5/2002 | Ono | G02B 21/02 359/356 |
| 6,859,331 | B2 * | 2/2005 | Kurata | G02B 21/02 359/656 |
| 7,215,478 | B1 * | 5/2007 | Hirata | G02B 21/33 359/656 |
| 8,243,129 | B2 * | 8/2012 | Uzawa | A61B 1/00096 359/657 |
| 8,773,765 | B2 * | 7/2014 | Sasamoto | G02B 7/08 359/649 |
| 8,958,154 | B2 * | 2/2015 | Taeko | G02B 21/02 359/566 |
| 2001/0007511 | A1 * | 7/2001 | Minami | G02B 23/2438 359/689 |
| 2001/0033425 | A1 * | 10/2001 | Kashima | G02B 21/02 359/656 |
| 2004/0252380 | A1 * | 12/2004 | Kashima | G02B 21/02 359/656 |
| 2006/0007558 | A1 * | 1/2006 | Hirata | G02B 21/33 359/656 |
| 2006/0087745 | A1 * | 4/2006 | Fahlbusch | G02B 21/33 359/656 |
| 2006/0215282 | A1 | 9/2006 | Hirata | |
| 2008/0239480 | A1 * | 10/2008 | Tomioka | G02B 23/2446 359/435 |
| 2009/0052062 | A1 | 2/2009 | Fujiwara | |
| 2009/0203963 | A1 | 8/2009 | Ito | |
| 2009/0284841 | A1 * | 11/2009 | Shi | G02B 21/02 359/656 |
| 2010/0182702 | A1 * | 7/2010 | Watanabe | G02B 21/33 359/656 |
| 2011/0036735 | A1 | 3/2011 | Yamaguchi | |

FOREIGN PATENT DOCUMENTS

| | | |
|---|---|---|
| JP | H01-307716 A | 12/1989 |
| JP | 2003-084214 A | 3/2003 |
| JP | 2006-023389 A | 1/2006 |
| JP | 2006-119300 A | 5/2006 |
| JP | 2006-227310 A | 8/2006 |
| JP | 2009-048085 A | 3/2009 |
| JP | 2009-192562 A | 8/2009 |
| JP | 2009-205063 A | 9/2009 |
| JP | 4608253 B2 | 1/2011 |
| JP | 2015-022262 A | 2/2015 |
| WO | 2009/035072 A1 | 3/2009 |

* cited by examiner

OBJECTIVE OPTICAL SYSTEM

CROSS-REFERENCE TO RELATED APPLICATIONS

This is a continuation of International Application PCT/JP2014/072868 which is hereby incorporated by reference herein in its entirety.

TECHNICAL FIELD

The present invention relates to an objective optical system, and, in particular, to an objective optical system having a small diameter and a high numerical aperture.

BACKGROUND ART

For example, when observing the inside of a living body, with microscopes, because the outer diameter of an objective lens is large, it is necessary to make a large incision in the living body for observation. However, making a large incision in the living body leads to high invasiveness, thus imposing an inordinate burden on the living body and making it impossible to perform observation for a long time. Furthermore, with general endoscopes, because the outer diameter is small, the invasiveness with respect to the living body is low, but, because the magnification is low, it is inadequate for observing the behavior of body tissue or molecules in a cell. Furthermore, with magnifying endoscopes, the magnification is high, but the numerical aperture (NA) on the object side is low, thus resulting in a lack of resolution and luminance.

Thus, as an objective optical system with which desired observation can be performed while achieving low invasiveness, for example, PTL 1 discloses an objective optical system in which the outer diameter at a distal end is relatively small, and the numerical aperture is large. According to this objective optical system, a small hole is formed in the living body, and the objective optical system is made to pass through this hole, thereby making it possible to observe the living body with low invasiveness.

CITATION LIST

Patent Literature

{PTL 1} Publication of Japanese Patent No. 4608253

SUMMARY OF INVENTION

Solution to Problem

According to one aspect, the present invention provides an objective optical system that is composed of a first group and a second group, in order from an object side, the first group including, in order from an object-side surface: a first lens that is, a single lens having a flat surface on the object side and a convex surface directed toward an image plane and having positive refractive power; a second lens that is a single lens having a convex surface directed toward the object and having positive refractive power; and a third lens that is a cemented lens in which a convex lens having a flat surface directed toward the object and a lens having negative refractive power are cemented and that has positive refractive power, and the second group including, in order from the object-side surface: a fourth lens that is a cemented lens in which a lens having negative refractive power and a double-convex lens are cemented; a fifth lens that is a cemented lens in which a lens having a concave surface directed toward the object and a lens having a convex surface directed toward the object are cemented; a sixth lens that is a cemented lens in which three lenses, i.e., a lens having negative refractive power, a lens having positive refractive power, and a lens having negative refractive power, are cemented and that has negative refractive power; and a seventh lens that is a compound lens having positive refractive power, wherein conditional expressions (1) and (2) are satisfied, $$0.57 < \text{abs}(M \times FL1G/LTL) < 0.63 \quad (1)$$

$$2.1 < |FL4/FL1G| < 2.4 \quad (2)$$

where M is a magnification of the entire objective optical system, LTL is the distance from an object surface to the image plane, and FL1G is a focal length of the first group.

DESCRIPTION OF EMBODIMENTS

An objective optical system according to one embodiment of the present invention will be described below with reference to the drawings.

Figure 1:
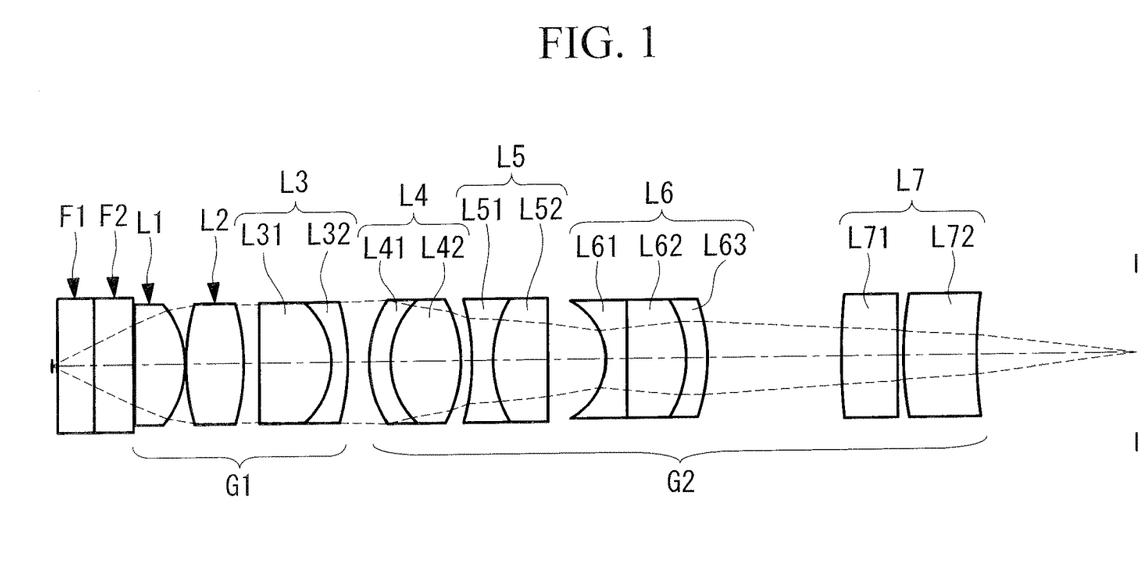
FIG. 1 is a sectional view showing the overall configuration of an objective optical system according to one embodiment of the present invention.

FIG. 1 is a sectional view showing the overall configuration of the objective optical system. As shown in FIG. 1, the objective optical system includes, in order from an object side, parallel plates F1 and F2, a first group G1, and a second group G2.

The parallel plates F1 and F2 adjust a working distance (WD) of the objective optical system.

The first group G1 converts light from an object into collimated light and includes, in order from an object-side surface, a first lens L1, a second lens L2, and a third lens L3.

The first lens L1 is a single lens that has a flat surface on the object side and a convex surface directed toward an image plane and that has positive refractive power. The second lens L2 is a single lens that has a convex surface directed toward the object and that has positive refractive power. The third lens L3 is a cemented lens in which a convex lens L31 having a flat surface directed toward the object and a lens L32 having negative refractive power are cemented and that has positive refractive power.

The second group focuses the collimated light from the first group G1 to correct aberrations and includes, in order from the object-side surface, a fourth lens L4, a fifth lens L5, a sixth lens L6, and a seventh lens L7.

The fourth lens L4 is a cemented lens in which a lens L41 having negative refractive power and a double-convex lens L42 are cemented. The fifth lens L5 is a cemented lens in which a lens L51 having a concave surface directed toward the object and a lens L52 having a convex surface directed toward the object are cemented. The sixth lens L6 is a cemented lens in which three lenses, i.e., a lens L61 having negative refractive power, a lens L62 having positive refractive power, and a lens L63 having negative refractive power, are cemented and has negative refractive power. The seventh lens L7 is a compound lens that includes a positive lens L71 and a positive lens L72 and that has positive refractive power.

Furthermore, the objective optical system is configured so as to satisfy the following conditional expressions.

$$0.57 < \text{abs}(M \times FL1G/LTL) < 0.63 \quad (1)$$

$$2.1 < |FL4/FL1G| < 2.4 \quad (2)$$

where M is the magnification of the entire objective optical system, LTL is the distance from an object surface to an image plane, and FL1G is the focal length of the first group G1.

The outer diameter of the objective optical system can be reduced by lowering the ray height of a ray passing through the fifth lens L5. In order to lower the ray height at the fifth lens L5, it is necessary to enhance the positive refractive power of the fourth lens L4. On the other hand, when the positive refractive power of the fourth lens is enhanced, the spherical aberrations on the object-side surface and the image-side surface of the fourth lens are increased. Thus, in order to lower the ray height at the fifth lens, it is necessary to enhance the positive refractive power of the fourth lens, to correct the spherical aberrations on the object-side concave surface of the fifth lens and on the object-side concave surface of the sixth lens, and to enhance the negative refractive power of the fifth lens.

The upper limit of the expression (1) is a value for limiting an increase in the ray height, which is caused by increasing the focal length of the first group, and the lower limit of the expression (1) is a value for successfully correcting the spherical aberration. Furthermore, the upper limit of the expression (2) is a value for reducing the ray height at the fifth lens by reducing the length of the fourth lens, and the lower limit of the expression (2) is a value for successfully correcting the spherical aberration.

Therefore, according to this embodiment, it is possible to achieve a high numerical aperture by successfully correcting the aberrations while having a smaller diameter.

Furthermore, the objective optical system is configured so as to satisfy the following expression (3), $$3.3 < |ndL51/r14| \times FLG2 < 4.9 \quad (3)$$

where ndL51 is the refractive index of a glass of the lens that has the concave surface directed toward the object, in the fifth lens, r14 is the radius of curvature of a surface of the fifth lens that is closest to the object, and FLG2 is the focal length of the second group.

The expression (3) is a conditional expression for the fifth lens so as to correct the spherical aberrations on the surface of the fifth lens that is closest to the object and on the surface of the sixth lens that is closest to the object. If the value exceeds the upper limit of the expression (3), aberrations are over-corrected, and, if the value is lower than the lower limit, spherical aberration correction cannot be performed.

The objective optical system is configured so as to satisfy conditional expression (4), $$10.8 < |ndL61/r17| \times FLG2 < 12.4 \quad (4)$$

where ndL61 is the refractive index at the d-line of the lens that is closest to the object, among the lenses of the sixth lens that have negative refractive power, r17 is the radius of curvature of the surface of the sixth lens that is closest to the object, and FLG2 is the focal length of the second group.

The expression (4) is a conditional expression for the sixth lens so as to correct the spherical aberrations on the surface of the fifth lens that is closest to the object and on the surface of the sixth lens that is closest to the object. If the value exceeds the upper limit of the expression (4), aberrations are over-corrected, and, if the value is lower than the lower limit, spherical aberration correction cannot be performed.

The objective optical system is configured so as to satisfy conditional expression (5), $$14 < vdL61/ndL61 - vdL62/ndL62 < 68 \quad (5)$$

where vdL61 is the Abbe number at the d-line of the lens that is closest to the object, among the lenses of the sixth lens that have negative refractive power, and ndL61 is the refractive index at the d-line of that lens. Furthermore, vdL62 is the Abbe number at the d-line of the lens that is located at the middle of the three lenses that constitute the sixth lens, and ndL62 is the refractive index at the d-line of that lens.

The expression (5) is a conditional expression for correcting chromatic aberration on the cemented surface between the negative lens on the object side and the positive lens, in the sixth lens. Specifically, the chromatic aberration can be corrected by setting appropriate values for the refractive index and the dispersive power of the positive lens, which is located at the middle in the sixth lens.

In this way, according to this embodiment, it is possible to provide a high-numerical-aperture objective optical system in which aberrations are successfully corrected while having a smaller diameter.

EXAMPLES

Figure 2:
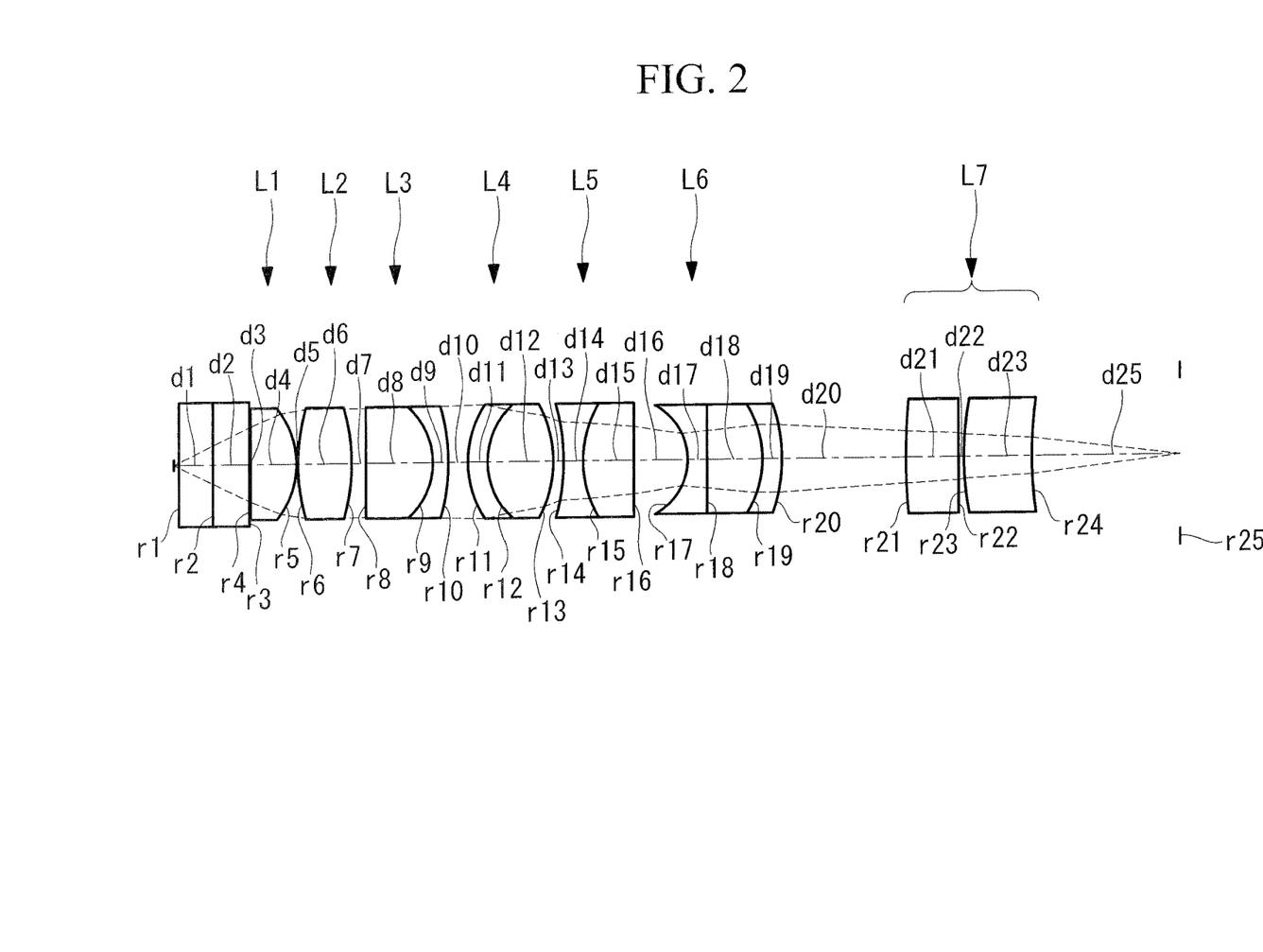
FIG. 2 is a sectional view showing the overall configuration of the objective optical system according to the embodiment of the present invention.

Next, Examples 1 to 5 of the objective optical system according to the above-described embodiment will be described with reference to FIGS. 3 to 12. In lens data to be described in each Example, r indicates the radius of curvature (unit mm), d indicates the intersurface spacing (mm), Nd indicates the refractive index at the d-line, and vd indicates the Abbe number at the d-line. Note that objective optical systems according to Examples 1 to 5 each have the lens construction shown in FIGS. 1 and 2.

Example 1

Figure 3:
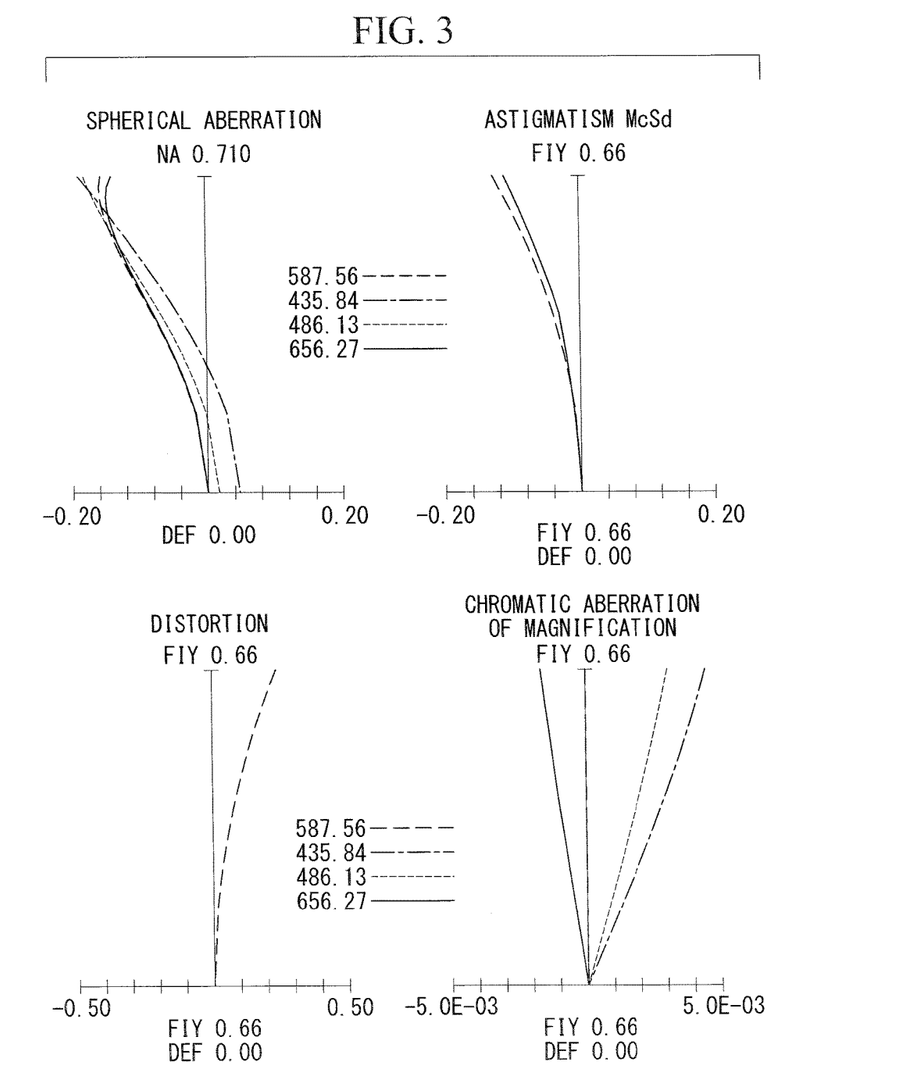
FIG. 3 shows aberration diagrams of an objective optical system according to Example 1 of the present invention.
Figure 4:
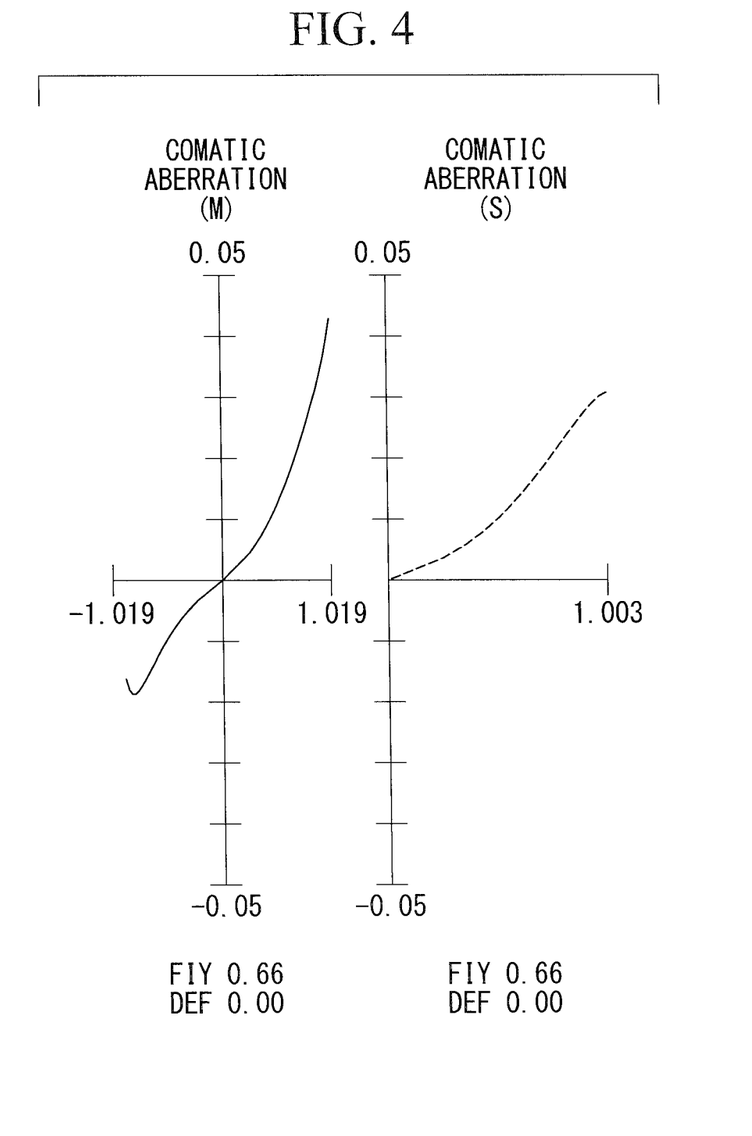
FIG. 4 shows aberration diagrams of the objective optical system according to Example 1 of the present invention.

FIGS. 3 and 4 show aberration diagrams of an objective optical system according to Example 1 of the present invention, and lens data of the objective optical system of Example 1 is shown below.

Example 2

| LENS DATA | | | | |
| --- | --- | --- | --- | --- |
| Surface Number | r | d | Nd | vd |
| Object Surface | ∞ | 0.108 | 1.35784 | 57.71 |
| 1 | ∞ | 0.570 | 1.45846 | 67.82 |
| 2 | ∞ | 0.770 | 1.88300 | 40.76 |
| 3 | ∞ | 0.030 | 1.00000 | |
| 4 | ∞ | 0.900 | 1.88300 | 40.76 |
| 5 | −1.705 | 0.050 | 1.00000 | |
| 6 | 5.805 | 1.050 | 1.43875 | 94.93 |
| 7 | −3.458 | 0.300 | 1.00000 | |
| 8 | ∞ | 1.450 | 1.43875 | 94.93 |
| 9 | −1.502 | 0.400 | 1.75500 | 52.32 |
| 10 | −3.718 | 0.400 | 1.00000 | |
| 11 | 2.380 | 0.400 | 1.75500 | 52.32 |
| 12 | 1.502 | 1.450 | 1.43875 | 94.93 |
| 13 | −2.297 | 0.308 | 1.00000 | |
| 14 | −4.302 | 0.400 | 1.84666 | 23.88 |
| 15 | 2.196 | 1.100 | 1.75500 | 52.32 |
| 16 | ∞ | 1.185 | 1.00000 | |
| 17 | −1.342 | 0.400 | 1.61340 | 44.27 |
| 18 | 10.191 | 1.100 | 1.84666 | 23.88 |
| 19 | −2.164 | 0.400 | 1.61340 | 44.27 |
| 20 | −3.519 | 2.600 | 1.00000 | |
| 21 | 16.756 | 1.050 | 1.52249 | 59.84 |
| 22 | ∞ | 0.100 | 1.00000 | |
| 23 | 5.007 | 1.000 | 1.75500 | 52.32 |
| 24 | 7.066 | 0.000 | 1.00000 | |
| 25 | ∞ | 1.870 | 1.00000 | |

Figure 5:
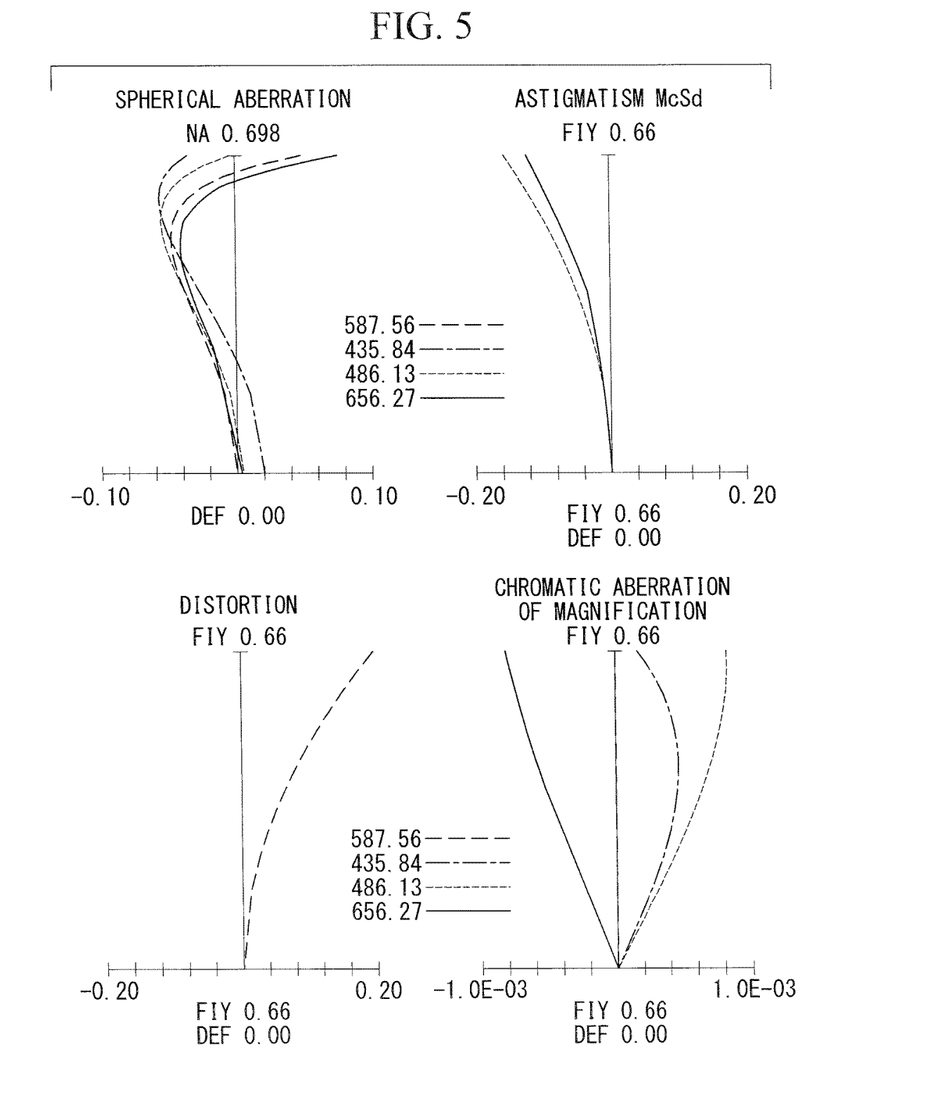
FIG. 5 shows aberration diagrams of an objective optical system according to Example 2 of the present invention.
Figure 6:
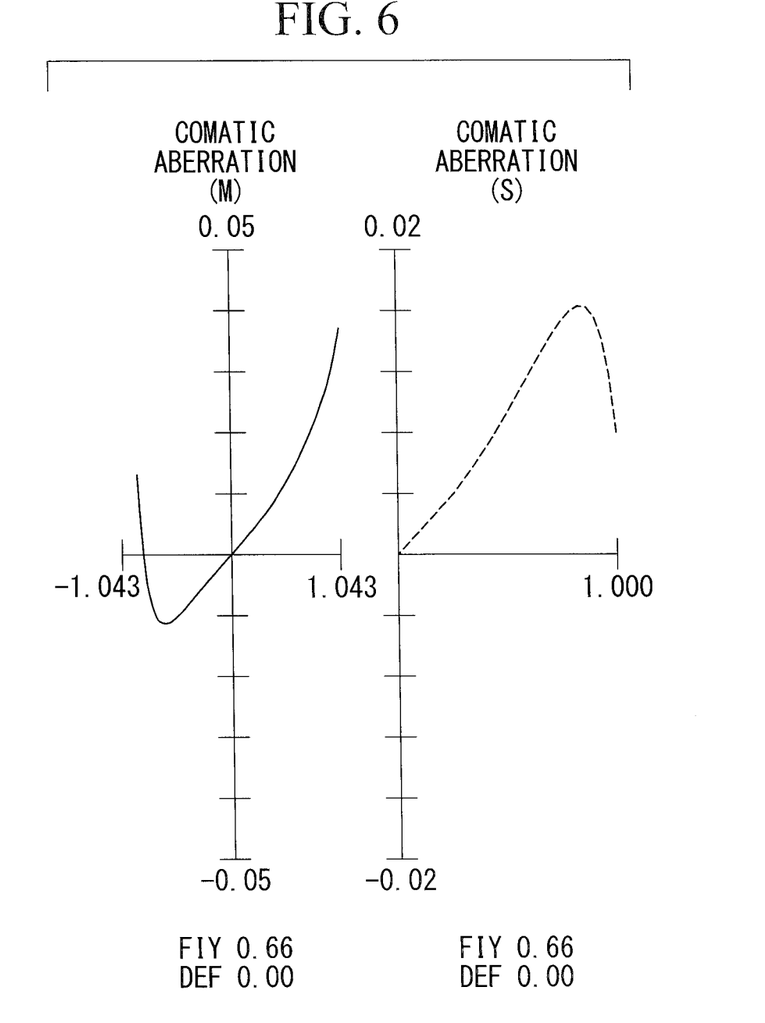
FIG. 6 shows aberration diagrams of the objective optical system according to Example 2 of the present invention.

FIGS. 5 and 6 show aberration diagrams of an objective optical system according to Example 2 of the present invention, and lens data of the objective optical system of Example 2 is shown below.

Example 3

| LENS DATA | | | | |
| --- | --- | --- | --- | --- |
| Surface Number | r | d | Nd | vd |
| Object Surface | ∞ | 0.074 | 1.35784 | 57.71 |
| 1 | ∞ | 0.570 | 1.45846 | 67.82 |
| 2 | ∞ | 0.770 | 1.88300 | 40.76 |
| 3 | ∞ | 0.030 | 1.00000 | |
| 4 | ∞ | 0.900 | 1.88300 | 40.76 |
| 5 | −1.680 | 0.050 | 1.00000 | |
| 6 | 7.107 | 1.050 | 1.43875 | 94.93 |
| 7 | −3.253 | 0.300 | 1.00000 | |
| 8 | ∞ | 1.450 | 1.43875 | 94.93 |
| 9 | −1.502 | 0.400 | 1.75500 | 52.32 |
| 10 | −3.822 | 0.400 | 1.00000 | |
| 11 | 2.436 | 0.400 | 1.75500 | 52.32 |
| 12 | 1.502 | 1.450 | 1.43875 | 94.93 |
| 13 | −2.297 | 0.310 | 1.00000 | |
| 14 | −5.080 | 0.400 | 1.84666 | 23.88 |
| 15 | 2.346 | 1.100 | 1.75500 | 52.32 |
| 16 | ∞ | 1.181 | 1.00000 | |
| 17 | −1.372 | 0.400 | 1.61340 | 44.27 |
| 18 | 9.014 | 1.100 | 1.84666 | 23.88 |
| 19 | −2.133 | 0.400 | 1.61340 | 44.27 |
| 20 | −3.480 | 2.600 | 1.00000 | |
| 21 | 17.534 | 1.050 | 1.52249 | 59.84 |
| 22 | ∞ | 0.100 | 1.00000 | |
| 23 | 5.027 | 1.000 | 1.75500 | 52.32 |
| 24 | 6.962 | 0.000 | 1.00000 | |
| 25 | ∞ | 1.870 | 1.00000 | |

Figure 7:
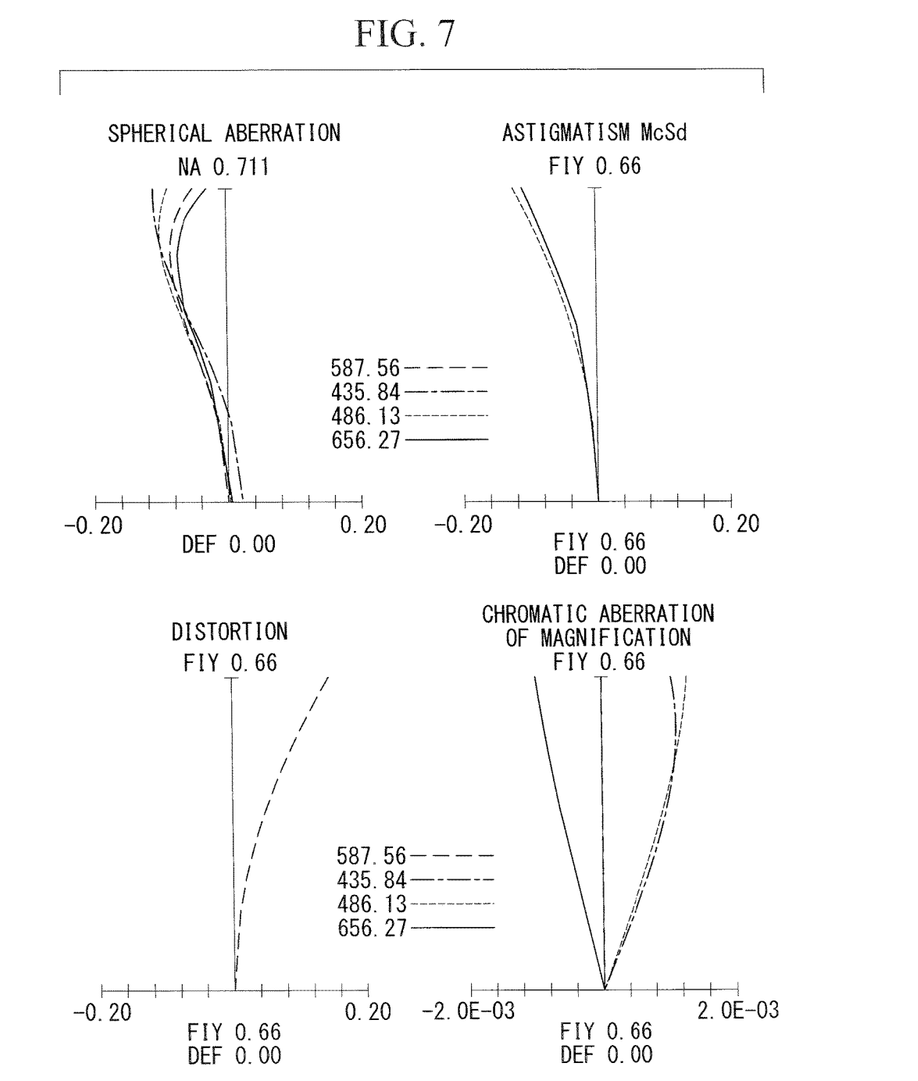
FIG. 7 shows aberration diagrams of an objective optical system according to Example 3 of the present invention.
Figure 8:
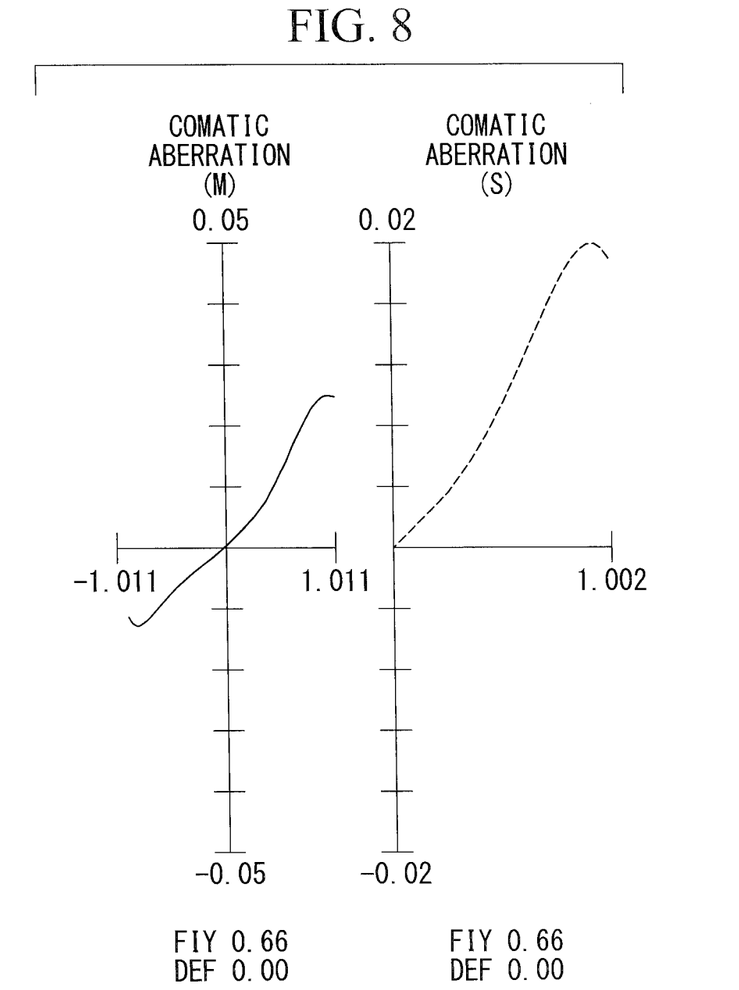
FIG. 8 shows aberration diagrams of the objective optical system according to Example 3 of the present invention.

FIGS. 7 and 8 show aberration diagrams of an objective optical system according to Example 3 of the present invention, and lens data of the objective optical system of Example 3 is shown below.

Example 4

| LENS DATA | | | | |
| --- | --- | --- | --- | --- |
| Surface Number | r | d | Nd | vd |
| Object Surface | ∞ | 0.076 | 1.35784 | 57.71 |
| 1 | ∞ | 0.570 | 1.45846 | 67.82 |
| 2 | ∞ | 0.770 | 1.88300 | 40.76 |
| 3 | ∞ | 0.030 | 1.00000 | |
| 4 | ∞ | 0.900 | 1.88300 | 40.76 |
| 5 | −1.723 | 0.050 | 1.0000 | |
| 6 | 5.618 | 1.050 | 1.43875 | 94.93 |
| 7 | −3.273 | 0.300 | 1.00000 | |
| 8 | ∞ | 1.450 | 1.43875 | 94.93 |
| 9 | −1.502 | 0.400 | 1.75500 | 52.32 |
| 10 | −3.434 | 0.400 | 1.00000 | |
| 11 | 2.368 | 0.400 | 1.75500 | 52.32 |
| 12 | 1.502 | 1.450 | 1.43875 | 94.93 |
| 13 | −2.297 | 0.299 | 1.00000 | |
| 14 | −3.745 | 0.400 | 1.84666 | 23.88 |
| 15 | 2.280 | 1.100 | 1.75500 | 52.32 |
| 16 | ∞ | 1.136 | 1.00000 | |
| 17 | −1.305 | 0.400 | 1.61340 | 44.27 |
| 18 | 8.516 | 1.100 | 1.84666 | 23.88 |
| 19 | −2.098 | 0.400 | 1.61340 | 44.27 |
| 20 | −3.444 | 2.600 | 1.00000 | |
| 21 | 15.028 | 1.050 | 1.52249 | 59.84 |
| 22 | ∞ | 0.100 | 1.00000 | |
| 23 | 4.876 | 1.000 | 1.75500 | 52.32 |
| 24 | 7.218 | 0.000 | 1.00000 | |
| 25 | ∞ | 1.870 | 1.00000 | |

Figure 9:
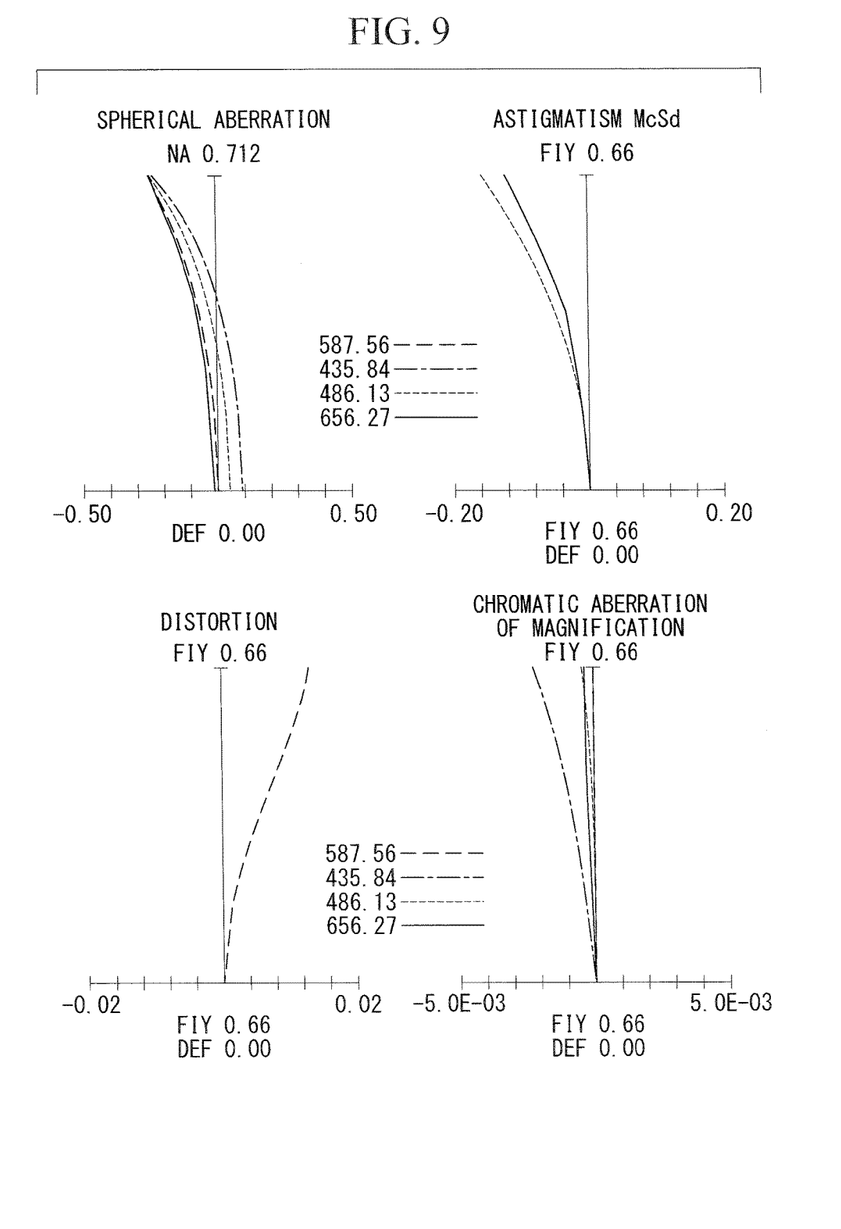
FIG. 9 shows aberration diagrams of an objective optical system according to Example 4 of the present invention.
Figure 10:
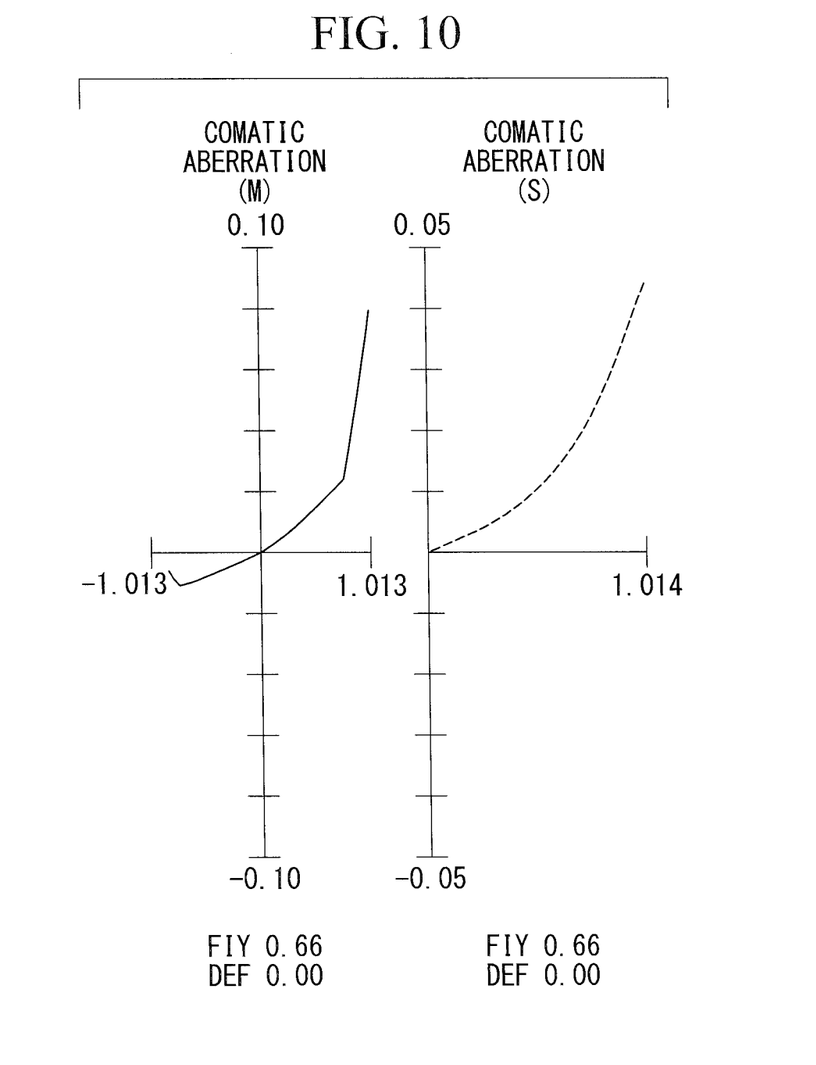
FIG. 10 shows aberration diagrams of the objective optical system according to Example 4 of the present invention.

FIGS. 9 and 10 show aberration diagrams of an objective optical system according to Example 4 of the present invention, and lens data of the objective optical system of Example 4 is shown below.

Example 5

| LENS DATA | | | | |
| --- | --- | --- | --- | --- |
| Surface Number | r | d | Nd | vd |
| Object Surface | ∞ | 0.099 | 1.35784 | 57.71 |
| 1 | ∞ | 0.460 | 1.45846 | 67.82 |
| 2 | ∞ | 0.902 | 1.88300 | 40.76 |
| 3 | ∞ | 0.030 | 1.00000 | |
| 4 | ∞ | 0.900 | 1.88300 | 40.76 |
| 5 | −1.731 | 0.050 | 1.00000 | |
| 6 | 7.105 | 1.050 | 1.43875 | 94.93 |
| 7 | −2.754 | 0.300 | 1.00000 | |
| 8 | ∞ | 1.433 | 1.43875 | 94.93 |
| 9 | −1.502 | 0.354 | 1.75500 | 52.32 |
| 10 | −4.310 | 0.385 | 1.00000 | |
| 11 | 2.405 | 0.400 | 1.75500 | 52.32 |
| 12 | 1.502 | 1.417 | 1.43875 | 94.93 |
| 13 | −2.237 | 0.301 | 1.00000 | |
| 14 | −4.684 | 0.400 | 1.84666 | 23.88 |
| 15 | 2.033 | 1.084 | 1.75500 | 52.32 |
| 16 | ∞ | 1.190 | 1.00000 | |
| 17 | −1.346 | 0.400 | 1.61340 | 44.27 |
| 18 | 10.596 | 1.097 | 1.84666 | 23.88 |
| 19 | −2.136 | 0.400 | 1.61340 | 44.27 |
| 20 | −3.439 | 2.593 | 1.00000 | |
| 21 | 15.778 | 1.030 | 1.52249 | 59.84 |
| 22 | ∞ | 0.100 | 1.00000 | |
| 23 | 5.003 | 0.978 | 1.75500 | 52.32 |
| 24 | 7.083 | 0.000 | 1.00000 | |
| 25 | ∞ | 3.000 | 1.00000 | |

Figure 11:
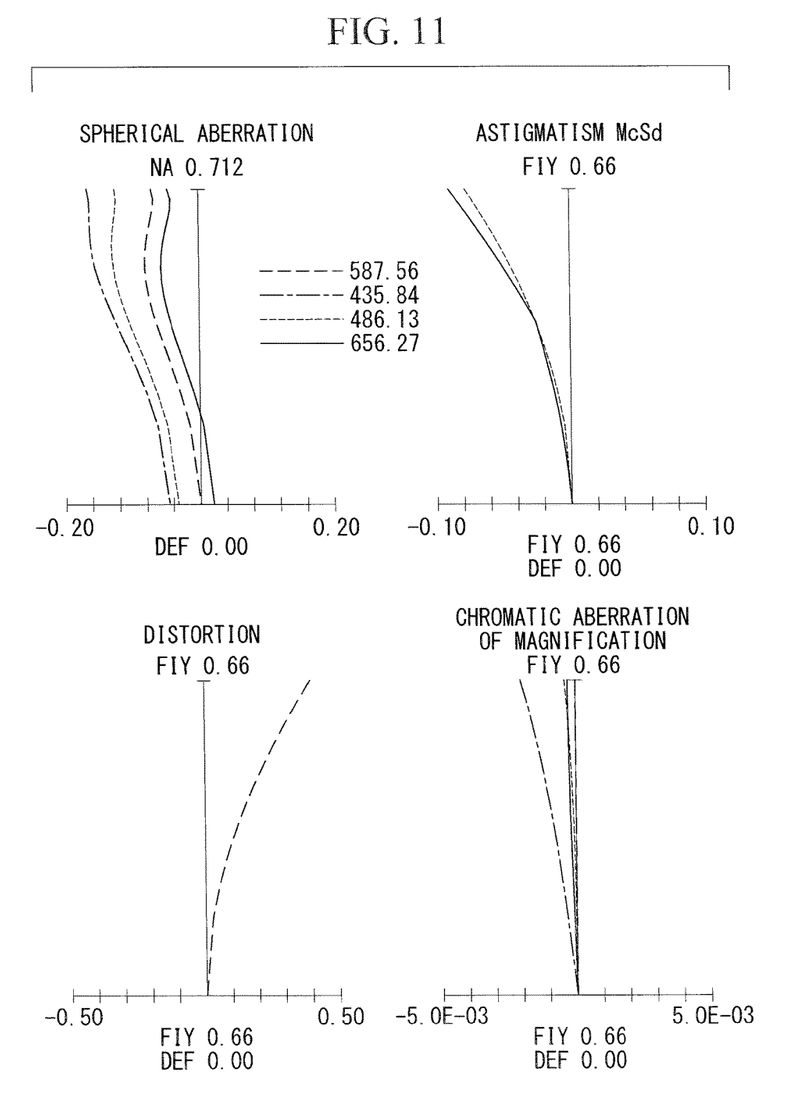
FIG. 11 shows aberration diagrams of an objective optical system according to Example 5 of the present invention.
Figure 12:
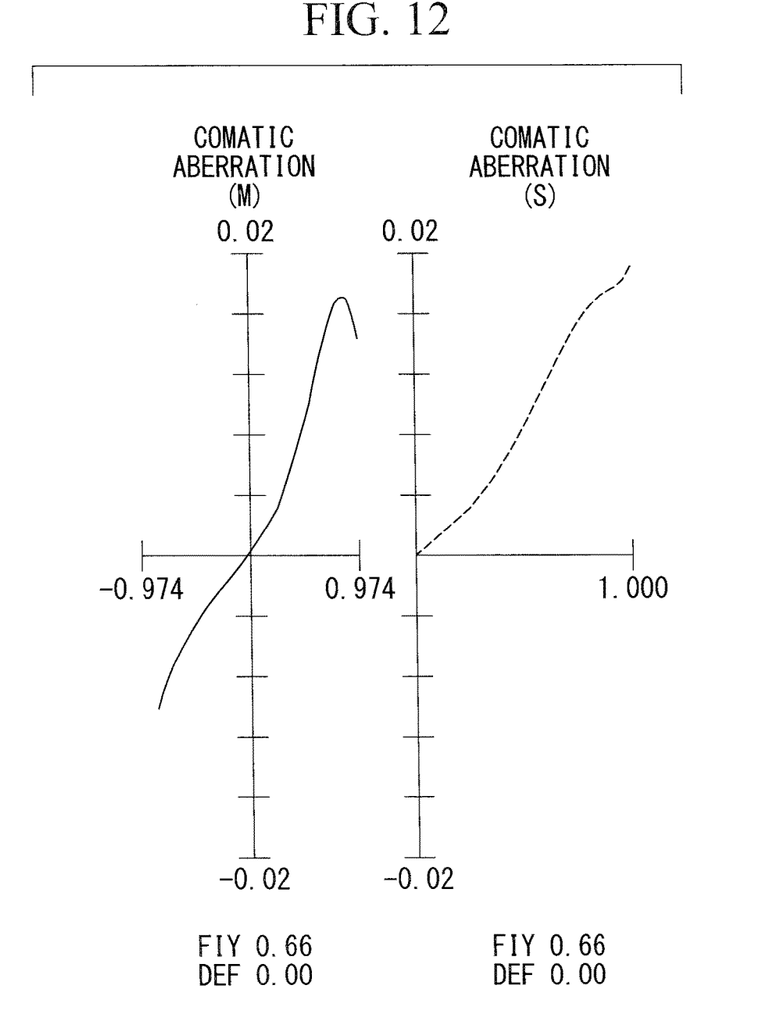
FIG. 12 shows aberration diagrams of the objective optical system according to Example 5 of the present invention.

FIGS. 11 and 12 show aberration diagrams of an objective optical system according to Example 5 of the present invention, and lens data of the objective optical system of Example 5 is shown below.

LENS DATA

| Surface Number | r | d | Nd | vd |
|---|---|---|---|---|
| Object Surface | ∞ | 0.104 | 1.35784 | 57.71 |
| 1 | ∞ | 0.700 | 1.45846 | 67.82 |
| 2 | ∞ | 0.740 | 1.88300 | 40.76 |
| 3 | ∞ | 0.030 | 1.0000 | |
| 4 | ∞ | 0.900 | 1.88300 | 40.76 |
| 5 | −1.777 | 0.050 | 1.00000 | |
| 6 | 3.853 | 1.050 | 1.43875 | 94.93 |
| 7 | −4.623 | 0.300 | 1.00000 | |
| 8 | ∞ | 1.350 | 1.43875 | 94.93 |
| 9 | −1.502 | 0.300 | 1.75500 | 52.32 |
| 10 | −4.021 | 0.400 | 1.00000 | |
| 11 | 2.256 | 0.400 | 1.75500 | 52.32 |
| 12 | 1.502 | 1.300 | 1.43875 | 94.93 |
| 13 | −2.297 | 0.200 | 1.00000 | |
| 14 | −3.937 | 0.400 | 1.84666 | 23.88 |
| 15 | 2.167 | 1.030 | 1.75500 | 52.32 |
| 16 | ∞ | 1.060 | 1.00000 | |
| 17 | −1.218 | 0.400 | 1.61340 | 44.27 |
| 18 | 27.609 | 1.100 | 1.84666 | 23.88 |
| 19 | −2.085 | 0.400 | 1.61340 | 44.27 |
| 20 | −3.219 | 2.480 | 1.00000 | |
| 21 | 11.003 | 1.110 | 1.52249 | 59.84 |
| 22 | ∞ | 0.100 | 1.00000 | |
| 23 | 5.060 | 1.340 | 1.75500 | 52.32 |
| 24 | 6.866 | 0.000 | 1.00000 | |
| 25 | ∞ | 3.000 | 1.00000 | |

Note that Table 1 shows various data in the configurations of the above-described Examples 1 to 5, and Table 2 shows values of the above-described expressions (1) to (5).

TABLE 1

| Sign | Example 1 | Example 2 | Example 3 | Example 4 | Example 5 |
|---|---|---|---|---|---|
| NA numerical aperture at object side | 0.7081 | 0.6976 | 0.7108 | 0.7021 | 0.7123 |
| M magnification | −6.2855 | −5.8252 | −6.1930 | −6.0860 | −5.9620 |
| FL1G focal length of first group | 1.5909 | 1.5861 | 1.6089 | 1.5532 | 1.5589 |
| LTL distance from surface closest to object to surface closest to image plane | 16.1029 | 16.1014 | 16.0443 | 15.9215 | 15.7300 |
| FL4 focal length of fourth lens | 3.6304 | 3.7086 | 3.6129 | 3.6041 | 3.4221 |

TABLE 2

| conditional expression | Example 1 | Example 2 | Example 3 | Example 4 | Example 5 |
|---|---|---|---|---|---|
| abs (M × FL1G/LTL) | 0.6210 | 0.5738 | 0.6210 | 0.5937 | 0.5909 |
| \| FL4/FL1G \| | 2.2820 | 2.3381 | 2.2455 | 2.3205 | 2.1952 |
| \| ndL51/r14 \| × FLG2 | 4.3283 | 3.3594 | 4.8582 | 3.7229 | 4.3597 |
| \| ndL61/r17 \| × FLG2 | 12.1197 | 10.8682 | 12.1771 | 11.3227 | 12.3120 |
| (vdL61)/(ndL61) − (vdL62)/(ndL62) | 14.5075 | 14.5075 | 14.5075 | 14.5075 | 14.5075 |

The above-described embodiment leads to the following inventions.

According to one aspect, the present invention provides an objective optical system that is composed of a first group and a second group, in order from an object side, the first group including, in order from an object-side surface: a first lens that is a single lens having a flat surface on the object side and a convex surface directed toward an image plane and having positive refractive power; a second lens that is a single lens having a convex surface directed toward the object and having positive refractive power; and a third lens that is a cemented lens in which a convex lens having a flat surface directed toward the object and a lens having negative refractive power are cemented and that has positive refractive power, and the second group including, in order from the object-side surface: a fourth lens that is a cemented lens in which a lens having negative refractive power and a double-convex lens are cemented; a fifth lens that is a cemented lens in which a lens having a concave surface directed toward the object and a lens having a convex surface directed toward the object are cemented; a sixth lens that is a cemented lens in which three lenses, i.e., a lens having negative refractive power, a lens having positive refractive power, and a lens having negative refractive power, are cemented and that has negative refractive power; and a seventh lens that is a compound lens having positive refractive power, wherein conditional expressions (1) and (2) are satisfied, $$0.57 < \mathrm{abs}(M \times FL1G/LTL) < 0.63 \tag{1}$$

$$2.1 < |FL4/FL1G| < 2.4 \tag{2}$$

where M is a magnification of the entire objective optical system, LTL is the distance from an object surface to the image plane, and FL1G is a focal length of the first group.

The upper limit of the expression (1) is a value for limiting an increase in the ray height, which is caused by increasing the focal length of the first group, and the lower limit of the expression (1) is a value for successfully correcting the spherical aberration. Furthermore, the upper limit of the expression (2) is a value for reducing the ray height at the fifth lens by reducing the length of the fourth lens, and the lower limit of the expression (2) is a value for successfully correcting the spherical aberration.

Therefore, according to this aspect, it is possible to achieve a high numerical aperture by successfully correcting the aberrations while achieving a smaller diameter.

In the above-described aspect, it is preferred that conditional expression (3) be satisfied, $$3.3 < |ndL51/r14| \times FLG2 < 4.9 \tag{3}$$

where ndL51 is the refractive index of a glass of the lens that has the concave surface directed toward the object, in the fifth lens, r14 is the radius of curvature of a surface of the fifth lens that is closest to the object, and FLG2 is the focal length of the second group.

The expression (3) is a conditional expression for the fifth lens so as to correct the spherical aberrations on the surface of the fifth lens that is closest to the object and on the surface of the sixth lens that is closest to the object. If the value exceeds the upper limit of the expression (3), aberrations are over-corrected, and, if the value is lower than the lower limit, spherical aberration correction cannot be performed.

Furthermore, in the above-described aspect, it is preferred that conditional expression (4) be satisfied, $$10.8 < |ndL61/r17| \times FLG2 < 12.4 \tag{4}$$

where ndL61 is the refractive index at the d-line of the lens that is closest to the object, among the lenses of the sixth lens that have negative refractive power, r17 is the radius of curvature of the surface of the sixth lens that is closest to the object, and FLG2 is the focal length of the second group.

The expression (4) is a conditional expression for the sixth lens so as to correct the spherical aberrations on the surface of the fifth lens that is closest to the object and on the surface of the sixth lens that is closest to the object. If the value exceeds the upper limit of the expression (4), aberrations are over-corrected, and, if the value is lower than the lower limit, spherical aberration correction cannot be performed.

Furthermore, in the above-described aspect, it is preferred that conditional expression (5) be satisfied, $$14 < vdL61/ndL61 - vdL62/ndL62 < 68 \quad (5)$$

where vdL61 is the Abbe number at the d-line of the lens that is closest to the object, among the lenses of the sixth lens that have negative refractive power, and ndL61 is the refractive index at the d-line of that lens. Furthermore, vdL62 is the Abbe number at the d-line of the lens that is located at the middle of the three lenses that constitute the sixth lens, and ndL62 is the refractive index at the d-line of that lens.

The expression (5) is a conditional expression for correcting chromatic aberration on the cemented surface between the negative lens on the object side and the positive lens, in the sixth lens. Specifically, the chromatic aberration can be corrected by setting appropriate values for the refractive index and the dispersive power of the positive lens, which is located at the middle in the sixth lens.

REFERENCE SIGNS LIST

G1 first group
G2 second group
L1 first lens
L2 second lens
L3 third lens
L4 fourth lens
L5 fifth lens
L6 sixth lens
L7 seventh lens

The invention claimed is:

1. An objective optical system that is composed of a first group and a second group, in order from an object side,
   the first group comprising, in order from an object-side surface:
   a first lens that is a single lens having a flat surface on the object side and a convex surface directed toward an image plane and having positive refractive power;
   a second lens that is a single lens having a convex surface directed toward the object and having positive refractive power; and
   a third lens that is a cemented lens in which a convex lens having a flat surface directed toward the object and a lens having negative refractive power are cemented and that has positive refractive power, and
   the second group comprising, in order from the object-side surface:
   a fourth lens that is a cemented lens in which a lens having negative refractive power and a double-convex lens are cemented;
   a fifth lens that is a cemented lens in which a lens having a concave surface directed toward the object and a lens having a convex surface directed toward the object are cemented;
   a sixth lens that is a cemented lens in which three lenses, that are a lens having negative refractive power, a lens having positive refractive power, and a lens having negative refractive power, are cemented and that has negative refractive power; and
   a seventh lens that is a compound lens having positive refractive power,
   wherein conditional expressions (1) and (2) are satisfied, $$0.57 < abs(M \times FL1G/LTL) < 0.63 \quad (1)$$

$$2.1 < |FL4/FL1G| < 2.4 \quad (2)$$

where M is a magnification of the entire objective optical system, LTL is the distance from an object surface to the image plane, and FL1G is a focal length of the first group.

2. An objective optical system according to claim 1, wherein conditional expression (3) is satisfied, $$3.3 < |ndL51/r14| \times FLG2 < 4.9 \quad (3)$$

where ndL51 is the refractive index of a glass of the lens that has the concave surface directed toward the object, in the fifth lens, r14 is the radius of curvature of a surface of the fifth lens that is closest to the object, and FLG2 is the focal length of the second group.

3. An objective optical system according to claim 1, wherein conditional expression (4) is satisfied, $$10.8 < |ndL61/r17| \times FLG2 < 12.4 \quad (4)$$

where ndL61 is the refractive index at the d-line of the lens that is closest to the object, among the lenses of the sixth lens that have negative refractive power, r17 is the radius of curvature of the surface of the sixth lens that is closest to the object, and FLG2 is the focal length of the second group.

4. An objective optical system according to claim 1, wherein conditional expression (5) is satisfied, $$14 < vdL61/ndL61 - vdL62/ndL62 < 68 \quad (5)$$

where vdL61 is the Abbe number at the d-line of the lens that is closest to the object, among the lenses of the sixth lens that have negative refractive power, ndL61 is the refractive index at the d-line of that lens, vdL62 is the Abbe number at the d-line of the lens that is located at the middle of the three lenses that constitute the sixth lens, and ndL62 is the refractive index at the d-line of that lens.

* * * * *